United States Patent [19]

Krempen et al.

[11] Patent Number: 5,415,777
[45] Date of Patent: May 16, 1995

[54] PROCESS FOR THE DECONTAMINATION OF SOILS CONTAMINATED BY PETROLEUM PRODUCTS

[75] Inventors: James P. Krempen; Charles S. Medbury, III, both of San Antonio, Tex.

[73] Assignee: Sunbelt Ventures, Inc., San Antonio, Tex.

[21] Appl. No.: 156,814

[22] Filed: Nov. 23, 1993

[51] Int. Cl.⁶ .............................................. C12S 1/00
[52] U.S. Cl. .................................. 435/262.5; 435/262; 210/606; 210/611; 210/632; 210/747; 405/128; 405/263; 134/26; 134/27; 134/28
[58] Field of Search ................ 405/128, 263, 264; 134/25.1, 26, 27, 28; 210/747, 751, 908, 925, 922, 611, 632, 606; 435/262.5, 281, 262

[56] References Cited

U.S. PATENT DOCUMENTS

| | | | |
|---|---|---|---|
| 4,521,515 | 6/1985 | Hata | 435/248 |
| 4,822,490 | 4/1989 | Dyadechko et al. | 210/611 |
| 4,841,998 | 6/1989 | Bruya | 134/10 |
| 4,906,302 | 3/1990 | Bruya | 134/10 |
| 4,913,586 | 4/1990 | Gabbita | 405/129 |
| 5,008,019 | 4/1991 | Trost | 210/747 |
| 5,035,537 | 7/1991 | Rose | 405/128 |
| 5,039,415 | 8/1991 | Smith | 210/611 |
| 5,051,030 | 9/1991 | Saha et al. | 405/128 |
| 5,055,196 | 10/1991 | Darian et al. | 210/638 |
| 5,059,252 | 10/1991 | Renfro | 134/7 |
| 5,096,600 | 3/1992 | Hoch | 210/751 |
| 5,100,455 | 3/1992 | Pinckard et al. | 71/9 |
| 5,126,073 | 6/1992 | Saab | 252/353 |
| 5,149,444 | 9/1992 | Hoch | 210/751 |
| 5,158,595 | 10/1992 | Stillman | 71/64.1 |
| 5,264,018 | 11/1993 | Koenigsberg et al. | 71/63 |
| 5,271,694 | 12/1993 | Cooper | 405/128 |
| 5,290,528 | 3/1994 | O'Conner et al. | 423/87 |
| 5,334,312 | 8/1994 | Lajoie | 210/610 |

FOREIGN PATENT DOCUMENTS 7406257  11/1974  Netherlands ........................ 210/922

*Primary Examiner*—Stanley S. Silverman
*Assistant Examiner*—Theodore McEwan Green
*Attorney, Agent, or Firm*—Cox & Smith Incorporated

[57] ABSTRACT

A method of decontaminating soil contaminated by petroleum products on the site of the contamination. Such decontamination is accomplished by chemical breakdown, enzymatic action and biological microbial degradation. Significant byproducts of this degradation of the hydrocarbon material are: water, sodium salts, ammonium salts, carbon dioxide, free amino acids and heat.

10 Claims, No Drawings

PROCESS FOR THE DECONTAMINATION OF SOILS CONTAMINATED BY PETROLEUM PRODUCTS

BACKGROUND OF THE INVENTION

1. Field of the Invention

The present invention relates to a process for decontaminating soils contaminated by petroleum products. Specifically, the invention relates to a method of treating contaminated soils by applying carbonate salts, ammonium hydroxide, and dilute organic acids to the soil at the site of the contamination. This can be followed by the addition of proteinase enzymes and bacterial inoculates.

2. Description of Related Art

Methods for treating soil contaminated by petroleum and its byproducts are previously known in the art. Such known methods have all had disadvantages relating to the fact that, in most cases, the contaminated soil must be excavated and transported to a decontamination site with a resulting increase in expense and time. Furthermore, most of the methods involve the addition of strong chemicals to the contaminated soil which themselves have the potential of being environmentally hazardous. Additionally, many of the known methods are not able to completely degrade the contaminating substances from soil, but instead, succeed only in separating the most hazardous of the contaminants from the soil in a form in which they can be more easily disposed of.

The Darian et al. patent, U.S. Pat. No. 5,055,196, discloses a process for treating soil or sludge to remove contaminants in contact with the soil or sludge. More particularly, the Darian et al. method relates to a process in which inorganic contaminants, such as metal or metal salts, or organic contaminants, such as PCBs, are removed from water-wet soil and sludge. Darian is apparently limited in its effectiveness to the treatment of soil contaminated with polychlorinated biphenyls (PCBs), polychlorinated dibenzodioxins (PCDDs), or polychlorinated dibenzofurans (PCDFs).

In particular, the Darian et al. method relates to both a process and apparatus for treating or cleaning a contaminated water-wet solid containing mixture by contacting the contaminated water-wet mixture with a solvent within an agitating reactor apparatus. The solvent contains a comminuting surfactant. The solvent used in the Darian method is chosen for its ability to dissolve the contaminant and is preferably a hydrocarbon that is sparingly soluble in water. A comminuting surfactant is added to the solvent to form a dispersed mixture of the solids, contaminants, and water. By this means the contaminant can be separated from the water-wet soil or sludge and subsequently the solvents and contaminants are separated and the solvent is reused. Considerable energy is used in the Darian et al. method, commencing with excavation of the contaminated soil and transportation to the Darian apparatus for processing. The transportation of the contaminated materials increases the chance of accidentally spreading the contamination while contributing substantially to the expense of the process. The use of a hydrocarbon solvent also increases the potential for actually creating an environmental hazard where the decontamination process is being performed.

The Smith patent, U.S. Pat. No. 5,039,415, relates to a method of treating hydrocarbon contaminated soil by excavating the soil, forming the soil into a flowing particulate stream; forming an aqueous liquid mixture of water and a microbe-containing solution that reacts with hydrocarbon to form $CO_2$ and water; dispersing the liquid mixture into the particulate soil stream to wet the particulate; and allowing the substance to react with the wetted soil particulate to thereby form $CO_2$ and water. The Smith process requires multiple cycles (4+) of the requisite mechanical handling and processing with the microbe-containing liquid mixture. Processes such as the Smith process require months of time and extensive capital investment to accomplish successful remediation of petroleum hydrocarbon soils.

The Gabbita patent, U.S. Pat. No. 4,913,586, describes a process and apparatus for safely handling and detoxifying contaminated soil substantially saturated with PH contaminants such as fuel and petroleum hydrocarbons. The contaminated soil is treated with an additive consisting of low grade humic acid and lime that is mixed with the soil in the approximate ratio of nine parts soil to one part of additive. The treatment involves breaking down the contaminated soil particles to a fine silt or sand, mixing the additive into the soil in a tumbler and, finally, discharging the thoroughly additive-covered and encapsulated toxic soil particles into a previously dug trench. In the Gabbita process, the potential for accidental release of the petroleum hydrocarbon contaminant remains should the encapsulation system breakdown. Furthermore the process requires the excavation and transportation of the contaminated soil to another site for treatment and the finding a disposal site for the encapsulated toxic soil.

The Saab patent, U.S. Pat. No. 5,126,073, discloses a method for treatment of solid and fluid materials contaminated by predominantly lipophilic harmful substances, in particular hydrocarbons and the like, especially oil-infested grounds and waters. Saab also discloses suitable systems and emulsifier substances for carrying out the method. The contaminated material is brought into a micro-dispersed, homogeneous emulsion where it is intimately mixed with at least one emulsifying substance as well as possibly with water. Subsequently, the emulsion is separated from the material while water is added and the emulsion is biologically decomposed. The treatment is conducted with an emulsifying composition containing biologically decomposable organic compounds, including a member with emulsification (causing lipophilic and hydrophilic functional groups), a fatty alcohol polyglycol ether-type tenside member and a member having one or more functional groups recognizable by bacterial cell membranes as being absorbable. The Saab method is expensive, time-consuming, labor-intensive and energy-intensive.

The Hoch patent, U.S. Pat. No. 5,149,444, reveals a method for treatment of soil, sediment or sludge containing toxic halogenated organic compounds (such as PCB's) and water. The method comprises the steps of mixing the soil, sediment, or sludge with a reagent (such as polyethylene glycol) capable of reacting with the halogenated compound. The mixture of soil, sediment, or sludge, and reagent is heated in a reaction zone to an elevated temperature thereby forming a reaction zone vapor stream containing at least a portion of the unreacted halogenated organic compound and water contained in the soil, sediment, or sludge. A portion of the reaction zone vapor stream is then condensed under conditions suitable for the formation of a condensate stream containing substantially all of the halogenated organic compound in the reaction zone vapor stream and a vapor stream containing water and trace amounts of the halogenated organic compound. The condensate stream is then recycled to the reaction zone and the resulting vapor stream is then treated to remove trace halogenated organic compound. The so treated stream is vented to the atmosphere; and the soil, sediment, or sludge containing less contaminant is removed from the reaction zone.

The Hoch '444 method's effectiveness is limited to the decontamination of soils, sediments, and sludges containing halogenated organic compounds. Hoch '444 requires the excavation of contaminated materials, relocation of the contaminated material to a reaction kiln, and heating the contaminated soil, sediments, or sludge to 300° C. under pressure to attain a change in state from liquid to vapor. Like Saab, the method is expensive, time-consuming, labor-intensive and energy-intensive. Furthermore, the use of polyethylene glycol introduces an added source of potential environmental hazard.

U.S. Pat. No. 5,008,0 19, the Trost method, is for treatment of water supply contamination. This patent discloses the method of flooding the contaminated formations with an alkaline solution of biodegradable polymers through various injection methods into a contaminated formation to divert, and/or remove contaminants. Decontaminated water is recovered through specific facilities. The Trost method is specifically for the decontamination of existing aquifers. Such decontamination is accomplished by a combination of flooding, injection, extraction and plugging using various alkaline polymer chemicals based on xanthan gum polymer. The extracts resulting from the Trost method must subsequently be treated and disposed of. The Trost method requires subsurface drilling and monitoring capacity along with vast quantities of water and several weeks of time.

The Rose patent, U.S. Pat. No. 5,035,537, discloses a method for treatment of soil, porous rock and similar material contaminated by petroleum, hydrocarbon and volatile organic compounds and includes the steps of gathering the contaminated soil, disbursing it uniformly on an impervious horizontal surface to a depth of four to six inches, treating it with an emulsifying agent and allowing the emulsifying agent to seep through the soil and volatilize the hydrocarbon and organic compounds in the soil. Optionally, the vapors emanating from the soil may be collected and burned.

Rose requires the excavation of contaminated solid materials, transportation of the materials to the site of a horizontal impervious surface where the decontamination process is performed. Furthermore, the Rose method emulsifies the contaminant and purports to volatilize it into the atmosphere both with and without the use of decreased atmospheric pressure. Thus Rose only serves to move the contaminants from the soil to the atmosphere in the hope that dilution with the free atmosphere is alone adequate degradation. Such a method, besides being labor-intensive and energy-intensive, is particularly hazardous in that it allows volatile organic chemicals to evaporate into the environment.

The Bruya patent, U.S. Pat. No. 4,841,998, concerns a method of decontaminating soil in which organic hazardous waste is removed from contaminated soil with an aqueous ammonia solution. The resulting aqueous ammonia solution containing organic hazardous waste is further processed to isolate the organic hazardous waste in a small volume for disposal. The treated soil is then returned to the excavation site without further processing. More specifically, the Bruya patent discloses that a broad range of hydrocarbon based contaminants can be removed from contaminated soil by means of excavation, crushing, screening, mixing with anhydrous ammonia and water (to form aqueous ammonia), settling, centrifugation, extraction of liquid, introduction of a suitable organic solvent, volatilization, extraction of ammonia and solvent by phase separation in which anhydrous ammonia is recycled to the aqueous ammonia mixing tank and the organic solvent is recycled and the extracted concentrate of contaminant is discharged for detoxification processing. As with other known methods, Bruya requires the steps of excavating, crushing and screening which are expensive, time-consuming, energy-intensive and labor-intensive. Furthermore, Bruya requires the handling of potentially dangerous anhydrous ammonia as both a cryogenic liquid and a highly pressurized gas. Additionally, Bruya requires elaborate mechanisms to create aqueous ammonia and then to recycle the ammonia. Additionally, the handling of expensive and potentially hazardous organic solvents such as hexane is also required. The resulting concentrated contaminant extract of the Bruya process must then be transported for final disposal by external means. Data cited in the Bruya process show that multiple treatments may be necessary to decrease the presence of contaminants from concentrations of 1000 ppm to less than 50 ppm.

The Renfro patent, U.S. Pat. No. 5,059,252, discloses a method for enhancing bioremediation which includes the step of applying a cationic ion exchange resin to the contaminated soil in an amount sufficient to promote growth of organisms capable of degrading the hazardous waste. The Renfro method is specifically intended to expedite the growth of certain bacteria and saprophytes and hasten the action of certain bacterial and saprophytic enzymes by acidifying hydrocarbon contaminants using a cationic ion exchange resin mixed with cyclic ring hydrocarbons covalently linked with a mineral acid but does not itself decontaminate or degrade the contaminants in hydrocarbon contaminated soils. The overall effect of the Renfro method is to acidify (decrease the pH of) contaminated soils to reduce the time (months or years) required of the aforementioned biological agents to accomplish bioremediation of the contaminating hydrocarbons. Thus the Renfro method does not directly accomplish decontamination of the soil but simply facilitates the natural bioremediation process which still takes months or years to accomplish.

The Hoch patent, U.S. Pat. No. 5,096,600, discloses a method for substantially degrading and detoxifying soils contaminated with halo organic compounds. The method comprises contacting a soil, sediment, or sludge containing less than 5% by weight of a halo organic contaminant, with a reagent of the formula MX, where M is a metal selected from the group consisting of K, Na, Ca, Zn, Mg, Ba, Pb, and X is hydroxide, carbonate, oxide, or acetate. The contact and subsequent reaction is carried out under conditions that insure the phase compatibility of the halo-organic contaminant and the reagent, which contact and subsequent reaction is preferably carded out under anhydrous conditions. The contact is carried out for a period of time sufficient to effect the dehalogenation of at least 90% of the contaminant.

Hoch '600, is limited in its effectiveness to the dehalogenation of (primarily intensely halogenated) halo-organic contaminants in soil, sediment or sludge. Decontamination by the Hoch method means the substantial removal (at least 90%) of the halogen atoms from compounds in the soil, thus yielding less toxic organic compounds (i.e. dichlorobiphenyl) or completely dehalogenated compounds. The resultant organic compounds are decreased in toxicity but require additional treatment with other processes or agents not a part of the Hoch method to finally render the contaminated soil fully decontaminated. The essential phase compatibility required to accomplish the Hoch method is accomplished by elevating the contaminated soil with the MX reagent to a temperature between one hundred eighty degrees Celsius (180° C.) and two hundred degrees Celsius (200° C.) with a quantity of the following phase compatibility agents and/or aprotic solvents acting in either or both capacities: (a) alcohols, including glycols, polyalkylene glycols, and polyols, (b) nitriles, (c) ethers, including polyethers, cyclic ethers, lower alkyl ethers of glycols, and lower alkyl ethers of polyalkylene glycols, (d) amines, and (e) amides. Without benefit of the above cited phase compatibility agents, the Hoch process requires the contaminated soil and reagent mixture to be elevated to the temperature of three hundred twenty degrees Celsius (320° C.). Thus, the Hoch method does not provide for the final degradation of hydrocarbon contaminants and requires follow-up processing. Furthermore, the method is time-consuming and expensive it requires an additional method of decontamination to break down the dehalogenated hydrocarbons.

The Bruya patent, U.S. Pat. No. 4,906,302, discloses a method for decontaminating the solid material contaminated by organic hazardous material which consists of forming an aqueous ammonia solution effective for removing organic hazardous waste from the contaminated material, contacting the material contaminated with organic hazardous waste with the aqueous ammonia solution to thereby transfer the organic hazardous waste from the material to the aqueous ammonia solution and separating the aqueous ammonia solution containing the organic hazardous waste from the material. Specifically, Bruya '302 discloses a method for decontaminating solids using an aqueous ammonia solution manufactured on site from anhydrous ammonia with an organic promoter (i.e., organic extracting solvent) from the group of pentane, hexane, heptane, octane, mineral oil, fuel off, toluene, Freon 113, 1,1,1-trichloroethane and mixtures of it. Thus, additional hydrocarbon materials are required to be brought into the contaminated site creating additional environmental hazards. Many of the organic promoters proposed by Bruya are demonstrated carcinogens, mutagens, and ozone depleters as well as being quite flammable. In the method as disclosed, it is necessary to recycle the ammonia and the organic promoters with additional environmental hazard. This recycling involves added time, expense and energy investment.

The present invention overcomes many of the various disadvantages encountered in methods known in the art, such as those described above, which have been used to decontaminate soil contaminated by hydrocarbons. The present invention's method of hydrocarbon decontamination of soils is principally accomplished by chemical breakdown of hydrocarbons. The decontamination can be further enhanced by the addition of protein enzymes. Biological microbes can be additionally added to enhance this decontamination process. The method can be accomplished on-site, thus avoiding the necessity of transporting the contaminated soil to another site. Chemical breakdown of the total parts of petroleum hydrocarbon occurs swiftly. Such breakdown can be continued by means of the proteinase enzymes and bacterial inoculate. Thus, the formerly contaminated soil becomes harmless to plant life within hours of treatment. Hydrocarbons treated with the process of the present invention are transformed into a water soluble state in which no toxic levels of hydrocarbons are detected. The process not only degrades toxic materials but does not render the soil sterile. Furthermore, the chemicals added to the soil to accomplish the decontamination are themselves biodegradable. Any hydrocarbon materials left over from the process are rendered more available to bacteria (both indigenous and otherwise) for further breakdown of the total parts of hydrocarbon. Thus, soil treated with the process of the present invention is left in a nutrient rich state for breakdown by bacteria, fungi and higher forms of plant life.

SUMMARY OF THE INVENTION

The present invention relates to a process of treating soil contaminated by petroleum products comprising the steps of:
(a) establishing a contained area of soil with horizontal and vertical boundaries;
(b) pulverizing the soil in the contained area to a uniform depth to distribute the contaminant evenly and to break up large particles;
(c) covering the soil with a layer of an anhydrous carbonate salt;
(d) applying a layer of dilute ammonium hydroxide to the soil;
(e) applying a layer of dilute organic acid to the soil;
(f) drying the soil by evaporation.

The present invention further relates to a process, as described above, wherein, after the soil is dried by evaporation, the process further comprises the steps of
(a) pulverizing the soil to a uniform depth to distribute remaining particles of contaminant evenly and to break up large particles; and
(b) applying to the soil an aqueous solution of proteinase enzymes or a combination of proteinase enzymes and inoculating bacteria.

Various other objects and advantages of the present invention will become apparent from the following detailed description of the invention.

DETAILED DESCRIPTION OF THE INVENTION

The process of the present invention is for the decontamination of soils contaminated by petroleum products. Such decontamination is accomplished by chemical breakdown, enzymatic action and biological microbial degradation. Significant byproducts of this degradation of the hydrocarbon material are: water, sodium salts, ammonium salts, carbon dioxide and heat. The chemical breakdown of the petroleum hydrocarbon occurs swiftly and the degradation is continued by means of the bacterial inoculate.

Hydrocarbons treated with this process are rendered less toxic to plant life very rapidly (within hours of treatment). Furthermore, they are rendered to a water soluble state for which no toxic levels are established. This product will not render the soil sterile. Residual hydrocarbon materials are rendered more available to bacteria (both indigenous and otherwise) for further breakdown of the total parts of hydrocarbon. Soft treated with the process chemistry is left in a nutrient rich state for bacteria, fungi and higher plant life. For example, when seed has been planted in treated soil, germination has occurred within twenty-four hours of completion of the final process without discernible effect to the plants. Testing has thus far shown that no toxic byproducts are produced. Thus, the soil becomes available to be used as it had been prior to contamination.

The present invention relates to a process of treating soil contaminated by petroleum products comprising the steps of:
(a) establishing a contained area of soil with horizontal and vertical boundaries;
(b) pulverizing the soil in the contained area to a uniform depth to distribute the contaminant evenly and to break up large particles;
(c) covering the soil with a layer of anhydrous carbonate salt;
(d) applying a layer of dilute ammonium hydroxide to the soil;
(e) applying a layer of dilute organic acid to the soil;
(f) drying the soil by evaporation.

The process of treating soil, as described above, can be supplemented by the following steps after the soil is dried by evaporation. These steps comprise:
(a) pulverizing the soil to a uniform depth to distribute remaining particles of contaminant evenly and to break up large particles; and
(b) applying to the soil an aqueous solution of proteinase enzymes or a combination of proteinase enzymes and inoculating bacteria.

In an embodiment of the present invention, the contaminated soil is excavated to establish an area of treatment having a depth of up to one foot.

After the treatment is applied, then samples of the soil can be taken at various time intervals, since the enzymatic action keeps on working for up to 30 days. It has been found that the treated soil is substantially free of contaminants within twenty-four hours.

In this same embodiment of the present invention, the carbonate salt used in the above process is selected from the group consisting of sodium carbonate, calcium carbonate, magnesium carbonate, potassium carbonate and lithium carbonate. In this embodiment, the carbonate salt is applied to the contaminated area to achieve a concentration of from one to twelve ounces of carbonate salt per square foot. In the most preferred embodiment, sodium carbonate is used.

In this same embodiment of the present invention, the ammonium hydroxide is diluted in water with one part ammonium hydroxide added to from eighteen to one hundred twenty eight parts water. The dilute aqueous ammonium hydroxide solution is applied to the contaminated area to achieve a concentration of from ten to one hundred ounces of dilute organic acid per square foot of soil.

In this same embodiment of the present invention, the organic acid used in the above process can be selected from the group consisting of citric acid, acetic acid, formic acid, benzoic acid, salicylic acid, oleic acid, oxaloacetic acid and a mixture of citric acid and acetic acid. In this embodiment, the organic acid is diluted in water with one part acid added to from eighteen to one hundred twenty eight parts water. The dilute aqueous organic acid solution is applied to the contaminated area to achieve the concentration of from ten to one hundred ounces of dilute organic acid per square foot of soil. In other embodiments, other carboxylic acids or dicarboxylic acids which naturally occur in soil can also be used.

The proteinase enzymes used in the above process can be selected from the group consisting of proteases, lipases, amylases, cellulases, catalases, carboxylases and endoglycosidases.

The inoculating bacteria used in the above process can be selected from the group consisting of Pseudomonas facultative hydrogen autotrophs and primary organisms.

Some examples of Pseudomonas facultative hydrogen autotrophs which can be used are: *Pseudomonas aeruginosa, Pseudomonas saccharophila, Pseudomonas facilis, Pseudomonas hydrogenovora, Pseudomonas hydrogenothermophila, Pseudomonas carboxydohydrogena, Pseudomonas compransoris, Pseudomonas carboxydovarans, Pseudomonas gasotropha,* and *Pseudomonas stanieri.*

Some examples of primary organisms which can be used are: Acetoanerobium, Acetobacterium, Acinetobacter, Bacillus, Haloarcula, Halobacterium, Haloferax, Natronbacterium, *Pseudomonas oleovorans, Pseudomonas butanovora, Pseudomonas lanceolata, Pseudomonas lemoignei, Pseudomonas luteola, Pseudomonas mendocina* and Kleibsella.

The process of treating soil, as described above, can be supplemented by the following steps after the step of applying proteinase enzymes and inoculating bacteria to the soil. These steps comprise:
(a) testing pH of soil surrounding the treated soil; and
(b) adjusting pH of the treated soil to match pH of surrounding soil by adding more of the dilute organic acid or the dilute ammonium hydroxide.

EXAMPLES

Example 1

Field Trial

Field trials were conducted at an oil pump site in June, 1993, southwest of Nixon, Tex. The site was an operating oil pump that had been leaking crude off from a broken seal. It was observed that the off contaminant was heavily concentrated around the pump jack. The area around the jack was stained a dark brown to black color and was spreading outward until a lighter brown color was predominant. The samples were taken by coring or drilling pilot holes over the entire area, ( a total of four holes were drilled in the well area, one being at the well head and another three feet from the well head, the last two were taken fifteen feet and sixty feet from the well head). The samples were tested to determine the extent and boundaries of the polluted area. The average amount of contamination of the soil around the well head was found to have a hydrocarbon contamination level of 103,000 TPH.

As soon as the boundary limits and concentration levels, as well as the types of contaminants were established, the work was started.

A layer of sodium carbonate was spread approximately one quarter of an inch thick over the entire area. After the sodium carbonate is applied to the soil, then ammonium hydroxide was mixed in water at a ratio of approximately one gallon of ammonium hydroxide to fifteen gallons of water. This solution was applied to the soil at a depth in the range of eight to twelve inches with a hose connected to a pump. The pump was connected to a water supply and a hopper which contained the ammonium hydroxide solution. The ammonium hydroxide and the sodium carbonate were than left on the ground to react with the hydrocarbons for a period of approximately one hour.

After one hour, a solution of concentrated acetic acid and citric acid in water, having a ratio of eight ounces of each acid to a gallon of water, was applied to the soil at a depth in the range of eight to twelve inches in the same manner as the ammonium hydroxide solution.

The treated soil was then allowed to dry for approximately 48 to 72 hours and broken up with a pulvermixer (such as those used to pulverize lime). An aqueous solution of proteinase enzyme was mixed with a ratio of 4 ounces of enzymes to each gallon of water. The enzymes were mixed in the hopper described above which was connected with a water pump and hose. (Alternatively, mixing of aqueous solutions can be accomplished in a water truck such as those used in the excavation business.) The enzymatic solution was applied to the dried, broken up soil at the rate of one gallon per two square feet of soil surface. A soil sample from the treated area was taken and tested twenty four hours after the enzymatic solution was applied and was found to have a hydrocarbon contamination level of 3180 TPH. (To achieve additional bioremediation of the soil, bacteria can be added at the time the enzyme solution is made in a ratio of 3 to 6 grams of bacteria per gallon).

Example 2

Laboratory application of the method of the invention

One hundred fifty pounds of a native rangeland soil was collected for use in the following test. Five gallons of Texas sweet light crude oil was procured from a crude off tank farm in southwest Texas and placed into a series of clean dry glass one gallon containers. The collected soil specimen was a dark reddish brown clay with gravel and sand. The soil specimen was spread to dry on a sunlight exposed concrete surface for a period of four hours.

When the specimen was judged to be in a standard surface-dry condition, the soil was mixed until homogeneous and sieved through a brass wire cloth $\frac{1}{4}''$ sieve. Material unable to pass through the sieve was discarded and consisted mostly of gravel with a few clods of clay that were not broken down. The soil which passed through the sieve was mixed until homogeneous and then one hundred pounds of the soil was measured into a container. Ten pounds of crude off was measured into a clean dry glass container. Two pounds of anhydrous sodium carbonate was measured into a clean dry glass container. Two gallons of water was measured into a clean dry glass container labeled ammonium hydroxide. Two gallons of water was poured into a clean dry glass container labeled acid mix. Sixteen fluid ounces of concentrated ammonium hydroxide was measured out and mixed until homogeneous into the glass container labeled ammonium hydroxide. Eight ounces of concentrated acetic acid was measured out and mixed into the glass container labeled acid mix. Ten ounces of dry weights citric acid crystals were measured out and mixed until homogeneous in the glass container labeled acid mix.

A clean dry polyethylene container having a two square foot surface was prepared for the test by having concentric rings of $\frac{1}{8}''$ holes drilled into the bottom. The upright container was placed on four 4"high standoffs in a six inch deep secondary container to capture any liquids which might percolate through the test specimen. A filter paper was used to line the test container and a quarter inch layer of coarse sand was laid over the paper. The one hundred pound container of dry sieved soil was introduced to a clean dry three cubic foot mechanically driven concrete mixer and gradually the ten pounds of crude oil was introduced. The mixer was run for a period of ten minutes until the soil and crude off had made a homogeneous mix.

Two samples of the homogeneous contaminated soil were collected and placed into clean dry glass containers labeled test 333, "Hot Sample." The samples were stored in a refrigerator at four degrees Celsius (4° C.). The contaminated soil was permitted to stand for one hour and then carefully placed into the test container in an approximately even layer.

The two pounds of sodium carbonate was spread over the surface of the contaminated soil within the test container in an approximately uniform layer. The ammonium hydroxide solution was then poured over the contaminated soil and sodium carbonate, contacting the entire surface. Immediately after introduction of the ammonium hydroxide solution, a light bubbling was observed at the soil surface and a temperature increase in the soil was also noted. The soil and chemicals were permitted to react for a period of one hour and then samples of the soil (label test 333 "S1") and leachate (label test 333"L1") were collected and placed into clean dry glass containers and stored at four degrees Celsius (4° C.). The acid mix solution was then carefully poured over the wet contaminated soil and permitted to react for a period of one hour. Immediately upon introduction of the acid mix to the contaminated soil an energetic evolution of $CO_2$ occurred, evidenced by a dark brown froth on the surface of the contaminated soil. After a period of one hour samples of the contaminated soil (labeled test 333 "S2") and leachate (labeled test 333 "L2") were collected and placed into clean dry glass containers and stored in a cooler at four (4°) degrees Celsius for further study.

Samples labeled test 333 S1 & S2 were taken within twenty-four hours of collection to a commercial laboratory and tested for the total recoverable petroleum hydrocarbon in accordance with the United States Environmental Protection Agency standard procedure 418.1. The wet soil was then spread on an impervious high density polyethylene liner on a horizontal concrete surface in the sun and was permitted to dry for eight hours. The polyethylene test container was cleaned and the filter paper and coarse sand discarded.

The mudcake was crushed by a wooden mallet, sieved through the $\frac{1}{4}''$ brass wire cloth sieve and remixed to a homogeneous state. The test soil was then put back into the cleaned test container using new filter paper and coarse sand. Twelve dry ounces of proteinase enzyme and bacterial inoculate were gradually added to two gallons of water and homogeneously mixed. The enzyme and bacterial inoculate solution were poured over the contaminated soil and permitted to react for a period of one hour. Samples of the soil (labeled test 333 "S3") and leachate (labeled test 333 "L3") were collected and stored in clean dry glass containers and stored in a refrigerator at four degrees Celsius (4° C.). Two gallons of water were measured and poured over the contaminated soil. Samples of the soil (labeled test 333 "S4") and leachate (labeled test 333 "L4") were collected and stored in clean dry glass containers and stored in a refrigerator at four degrees Celsius (4° C.).

The treated soil pH was then rebalanced to the level of the native soil.

Analysis of the "Hot Sample" and sample "S4" indicated that the original contamination level was 90,000 parts per million and had been decreased to a level of 210 parts per million total recoverable petroleum hydrocarbon.

While the foregoing invention has been described in some detail for purposes of clarity and understanding, it will be clear to one skilled in the art from a reading of this disclosure that various changes in form and detail can be made without departing from the true scope of the invention. All publications cited in this application are specifically incorporated by reference herein.

We claim:

1. A process of treating soil contaminated by petroleum products comprising the steps of:
   (a) establishing a contained area of soil with horizontal and vertical boundaries;
   (b) pulverizing the soil in the contained area to a uniform depth to distribute the contaminant evenly and to break up large particles;
   (c) covering the soil with a layer of an anhydrous carbonate salt;
   (d) applying a layer of dilute ammonium hydroxide to the soil to dissolve the carbonate salt in the ammonium hydroxide, thus forming a solution, and leaving the solution to sit on the soil for a period sufficient to let the solution mix with the soil;
   (e) applying a layer of dilute organic acid to the soil mixed with the solution;
   (f) drying the soil to which the solution and the acid has been applied by evaporation for a period sufficient to let the soil harden.

2. A process of treating soil according to claim 1, wherein the anhydrous carbonate salt is selected from the group consisting of sodium carbonate, calcium carbonate, magnesium carbonate, lithium carbonate and potassium carbonate.

3. A process of treating soil according to claim 1, wherein the organic acid is selected from the group consisting of citric acid, acetic acid, oxaloacetic acid, formic acid, benzoic acid, salicylic acid, oleic acid and a mixture of citric acid and acetic acid.

4. A process of treating soil according to claim 1, wherein, after the soil is dried by evaporation, the process further comprises the steps of
   (a) pulverizing the soil to a uniform depth to distribute remaining particles of contaminant evenly and to break up large particles; and
   (b) applying an aqueous solution comprising proteinase enzymes to the soil.

5. A process of treating soil according to claim 4, wherein the proteinase enzymes are selected from the group consisting of proteases, lipases, amylases, cellulases, catalases, carboxylases and endoglycosidases.

6. A process of treating soil according to claim 4, wherein the aqueous solution applied to the pulverized soil further comprises inoculating bacteria.

7. A process of treating soil according to claim 6, wherein the inoculating bacteria is selected from the group consisting of Pseudomonas facultative hydrogen autotrophs and primary organisms.

8. A process according to claim 7 wherein the Pseudomonas facultative hydrogen autotrophs are selected from the group consisting of *Pseudomonas aeruginosa, Pseudomonas saccharophila, Pseudomonas facilis, Pseudomonas hydrogenovora, Pseudomonas hydrogenothermophila, Pseudomonas carboxydohydrogena, Pseudomonas compransoris, Pseudomonas carboxydovarans, Pseudomonas gasotropha,* and *Pseudomonas stanieri.*

9. A process according to claim 7 wherein the primary organisms are selected from the group consisting of Acetoanerobium, Acetobacterium, Acinetobacter, Bacillus, Haloarcula, Halobacterium, Haloferax, Natronbacterium, *Pseudomonas oleovorans, Pseudomonas butanovora, Pseudomonas lanceolata, Pseudomonas lemonoignei, Pseudomonas luteola, Pseudomonas mendocina* and Kleibsella.

10. A process of treating soil according to claim 5, wherein, after the aqueous solution comprising proteinase enzymes is applied to the soil, the process further comprises the steps of
   (a) testing pH of soil surrounding the treated soil; and
   (b) adjusting pH of the treated soil to match pH of surrounding soil by adding more of the dilute organic acid or the dilute ammonium hydroxide.

* * * * *